United States Patent [19]

Badmin et al.

[11] 4,125,613
[45] Nov. 14, 1978

[54] PESTICIDAL CINNOLINES

[75] Inventors: John S. Badmin, Isle of Sheppey; Richard F. Jones, Faversham, both of England

[73] Assignee: Shell Oil Company, Houston, Tex.

[21] Appl. No.: 867,419

[22] Filed: Jan. 6, 1978

[30] Foreign Application Priority Data

Jan. 10, 1977 [GB] United Kingdom ............... 718/77

[51] Int. Cl.$^2$ ............................................. A61K 31/495
[52] U.S. Cl. ............................................................ 424/250
[58] Field of Search ........................ 260/250 C; 424/250

Primary Examiner—Albert T. Meyers
Assistant Examiner—H. Steven Seifert

[57] ABSTRACT

Use of certain cinnolines as pesticides and pesticidal compositions containing them.

2 Claims, No Drawings

PESTICIDAL CINNOLINES

DESCRIPTION OF THE INVENTION

It has been found that certain cinnolines have insecticidal and/or acaricidal properties, some being of interest for controlling ticks. These cinnolines, eleven in number, are described by the formula:

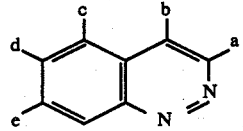

(I)

wherein a, b, c, d and e are as follows:

| Compound No. | a | b | c | d | e |
|---|---|---|---|---|---|
| (1) | H | H | H | H | H |
| (2) | H | —COOH | H | H | H |
| (3) | H | —OH | H | Br | H |
| (4) | Br | H | H | H | H |
| (5) | H | H | H | H | Cl |
| (6) | H | H | Cl | H | H |
| (7) | H | —CH$_3$ | H | H | H |
| (8) | —CH$_3$ | —C$_2$H$_5$ | H | H | H |
| (9) | —CH$_3$ | —OH | H | H | H |
| (10) | —CH$_3$ | —COOCH$_3$ | H | H | H |
| (11) | —CH$_3$ | H | H | H | H |

The invention accordingly comprises the use of these compounds as insecticides and/or acaricides and insecticidal and/or acaricidal compositions containing sufficient amounts of them to control such pests, together with a carrier or both a carrier and a surface-active agent.

The term 'carrier' as used herein means a solid or fluid material, which may be inorganic or organic and of synthetic or natural origin, with which the active compound is mixed or formulated to facilitate its application to the plant, seed, soil, animal, or other object to be treated, or its storage, transport or handling. The carrier may be a solid or a fluid. Any of the materials usually applied in formulating pesticides may be used as the carrier.

Suitable solid carriers are natural and synthetic clays and silicates, for example natural silicas such as diatomacious earths; magnesium silicates, for example, talcs; magnesium aluminum silicates, for example, attapulgites and vermiculites; aluminum silicates, for example, kaolinites, montmorillonites and micas; calcium carbonate; calcium sulphate; synthetic hydrated silicon oxides and synthetic calcium or aluminum silicates; elements such as for example, carbon and sulphur; natural and synthetic resins such as, for example coumarone resins, polyvinyl chloride and styrene polymers and copolymers; solid polychlorophenols; bitumen; waxes such as for example, beeswax, paraffin wax, and chlorinated mineral waxes; and solid fertilizers, for example superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene, petroleum fractions such as for example, kerosine, light mineral oils, chlorinated hydrocarbons, such as for example, carbon tetrachloride, perchloroethylene, trichloroethane, including liquefied normally vaporous gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides, fungicides, or insecticides may be used. Examples of suitable surfaceactive agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example, sodium lauryl sulphate, sodium secondary alkyl sulphates, sodium salts of sulphurated castor oil, and sodium alkylaryl sulphonates such as sodium dodecylbenzene sulphonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols and will generally contain 0.5 to 95% by weight, preferably 0.5 to 75% by weight, of toxicant. Wettable powders are usually compounded to contain 25, 50 or 75% by weight of toxicant and usually contain, in addition to solid carrier, 3–10% by weight of a dispersing agent and, where necessary, 0–10% by weight of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally, granules will contain ½–25% by weight toxicant and 0–10% by weight of additives such as stabilizers, slow release modifiers and binding agents. Emulsifiable concentrates usually contain, in addition to the solvent and, when necessary, co-solvent, 10–50% w/v toxicant, 2–20% w/v emulsifiers and 0–20% w/v of appropriate additives such as stabilizers, penetrants and corrosion inhibitors. Suspension concentrates are compounded so as to obtain a stable, non-sedimenting, flowable product and usually contain 10–75% by weight toxicant, 0.5–15% by weight of dispersing agents, 0.1–10% by weight of suspending agents such as protective colloids and thixotropic agents, 0–10% by weight of appropriate additives such as defoamers, corrosion inhibitors, stabilizers, penetrants and stickers, and as carrier, water or an organic liquid in which the toxicant is substantially insoluble; certain organic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oilin-water type, and may have a thick "mayonnaise"-like consistency.

The compositions of the invention may also contain other ingredients for example, other compounds possessing pesticidal, for example insecticidal, acaricidal, herbicidal or fungicidal properties.

The cinnoline derivatives of Formula I may be prepared by methods known per se in the literature, for example, the methods disclosed in:

J. Chem. Soc., 1953, 609;
J. Am Chem. Soc., 68, 1310, (1946);
J. Chem. Soc. (C), 1968, 2621;
J. Chem. Soc., 1956, 4207;
J. Chem. Soc., 1959, 2366; and
J. Chem. Soc., 1948, 354.

The invention is further illustrated by reference to the following examples:

EXAMPLE 1

Pesticidal Activity

The insecticidal and acaricidal activity of the compounds according to the present invention was tested as follows:

The compounds as shown in Table I were formulated as solutions or suspensions in water containing 20% by weight of acetone and 0.05% by weight of Triton X 100 as wetting agent. The formulations contained 0.6% by weight of the compounds to be tested. Broad bean plants, trimmed to one leaf each, were sprayed on the under-surface of the leaf with the above formulation, spraying with a spraying machine delivering 450 liters per hectare, the plants passing under the spray on a moving belt. Ten apterous (6 day old) vetch aphids (Megoura viciae - M.v.) were placed on the sprayed leaf of each broad bean plant. The plants were then enclosed in glass cylinders fitted at one end with a muslin cap. Mortality counts were made after 24 hours.

In tests against glass house spider mites (*Tetranychus urticae* - T.u.) leaf discs cut from French bean plants were sprayed in the manner described above. One hour after spraying, the discs were inoculated with 10 adult mites. Mortality counts were made 48 hours after inoculation.

The results of the tests against *Megoura viciae* and *Tetranychus urticae* were graded according to the following scheme:

Grade 0 = less than 50% mortality at 0.6% active ingredient in spray.
Grade 1 = 50% mortality at a concentration range $\leq 0.6$ to $> 0.2\%$ active ingredient in spray.
Grade 2 = 50% mortality at a concentration range $\leq 0.2$ and $> 0.06\%$ active ingredient in spray.
Grade 3 = 50% mortality at a concentration range $\leq 0.06$ and $> 0.02\%$ active ingredient in spray.
Grade 4 = 50% mortality at a concentration range $\leq 0.02$ and $> 0.06\%$ active ingredient in spray.

The results are shown in Table I.

Table I

| Compound No. | Pesticidal Grades | |
|---|---|---|
| | M.v. | T.u. |
| 1 | 3 | 4 |
| 2 | 0 | 2 |
| 3 | 1 | 0 |
| 4 | 3 | 1 |
| 5 | 1 | 3 |
| 6 | 3 | 1 |
| 7 | 3 | 4 |
| 8 | 2 | 1 |
| 9 | 1 | 0 |

Table I-continued

| Compound No. | Pesticidal Grades | |
|---|---|---|
| | M.v. | T.u. |
| 10 | 2 | 1 |
| 11 | 0 | 1 |

EXAMPLE 2

Tickicidal Activity

(a) Larvae

The compounds shown in Table II were formulated as solutions or fine suspensions in acetone containing 10% by weight of polyethylene glycol having an average molecular weight of 400. The formulations contained 0.1% by weight of the compound to be tested. 1 milliliter of the above-mentioned solution was applied evenly to a filter paper situated inside a petri dish. After the paper was sufficiently dry it was folded in half and partly crimped along the outer edge to form a packet. About 80–100 larvae of the cattle tick (*Boophilus microplus*) were transferred into the packet which was then sealed completely. The packets were placed inside an incubator, maintained at 27° C. and 80% relative humidity, before assessing mortality 24 hours later.

Firstly, the compounds were rated according to the following scheme:
A $\geq 90\%$ mortality
B 80–30% mortality
C $\leq 20\%$ mortality Then, those compounds gaining an A rating were subjected to further testing to determine the lethal concentration to kill 50% of the pest (LC$_{50}$); four concentrations were applied to obtain a dosage/mortality curve and each test was repeated 2 or 3 times. The toxicity of the compound is compared with that of a standard insecticide (parathion) and expressed as a Toxicity Index (TI).

$$TI = \frac{LC_{50} \text{ of standard}}{LC_{50} \text{ of compound}} \times 100$$

(b) Adults

For initial tests a 5% solution of the compound was prepared in acetone. For secondary tests with active compounds, half dilutions were prepared in acetone, to span the estimated LD$_{50}$.

Fully engorged female ticks (*Boophilus microplus*) were placed ventral side uppermost in a petri dish. Each test solution was taken up in a micrometer syringe and a 2 microliter droplet of solution applied to the ventral abdomen of each tick. Twelve ticks were treated with each solution both in initial and secondary tests.

Treated ticks were stored (for fourteen days) in an incubator maintained at 27° C. and 80% relative humidity. The reduction in the amount of eggs produced during this period was assessed and the eggs were retained for a further period to estimate the percentage hatch.

In initial tests, compounds were rated:
A $\geq 90\%$ reduction is egg mass
B 80–30% reduction in egg mass
C $\leq 20\%$ reduction in egg mass Compounds rated A are passed for an LD$_{50}$ determination, four concentrations being applied to obtain a dosage/response curve and the test repeated 2 or 3 times.

The toxicity of a compound is compared with that of the standard parathion and expressed as a Toxicity Index (TI).

$$\text{Toxicity Index} = \frac{LD_{50} \text{ of standard}}{LD_{50} \text{ of compound}} \times 100$$

The results for larvae and adult ticks are shown in Table II.

The tests included a strain of mites (Mount Alford strain) that is known to be resistant to the action of organophosphorus (O-P) compounds, and a strain that is known not to be resistant to the action of such compounds. Also shown in Table II is the Resistance Factor for each of the compounds tested which is defined as follows:

$$\text{Resistance Factor} = \frac{LC_{50} \text{ against } O-P \text{ resistant strain}}{LC_{50} \text{ against susceptible strain}}$$

Table II

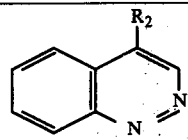

Activity Against the Susceptible and Mount Alford OP-Resistant Strains of the Cattle Tick (Boophilus Microplus)

| Active Ingredient Compound No. | Larva | | Adult | |
|---|---|---|---|---|
| | Toxicity Index | Resistance Factor | Toxicity Index | Resistance Factor |
| 1 | 51 | 1 | 25 | 1 |
| 7 | 42 | 1 | 57 | 1 |
| 2 | B | — | C | — |
| Parathion | 100 | 220 | 100 | 110 |

What is claimed is:

1. A method for killing insect and acarid pests which comprises applying to a locus infested by said pests an effective amount of one of eleven cinnolines of the formula (I)

wherein, respectively, a, b, c, d, and e are:

| a | b | c | d | e |
|---|---|---|---|---|
| H | H | H | H | H |
| H | —COOH | H | H | H |
| H | —OH | H | Br | H |
| Br | H | H | H | H |
| H | H | H | H | Cl |
| H | H | Cl | H | H |
| H | —CH$_3$ | H | H | H |
| —CH$_3$ | —C$_2$H$_5$ | H | H | H |
| —CH$_3$ | —OH | H | H | H |
| —CH$_3$ | —COOCH$_3$ | H | H | H |
| —CH$_3$ | H | H | H | H |

2. A method according to claim 1 in which the cinnoline is one in which b is methyl and a, c, d and e, each, is hydrogen.

* * * * *